(12) United States Patent
Bear

(10) Patent No.: US 7,226,619 B1
(45) Date of Patent: Jun. 5, 2007

(54) MATERIAL FOR CONTROLLING DIVERSION OF MEDICATIONS

(75) Inventor: David Bear, Wellesley, MA (US)

(73) Assignee: PharmoRx Inc., Wellesley, MA (US)

( * ) Notice: Subject to any disclaimer, the term of this patent is extended or adjusted under 35 U.S.C. 154(b) by 0 days.

(21) Appl. No.: 10/935,506

(22) Filed: Sep. 7, 2004

(51) Int. Cl.
    *A61K 9/00* (2006.01)
    *A61K 8/02* (2006.01)
    *A61K 9/14* (2006.01)
    *A61K 9/16* (2006.01)

(52) U.S. Cl. .................. 424/489; 424/401; 424/490
(58) Field of Classification Search ............... 424/490, 424/489, 401
See application file for complete search history.

(56) References Cited

U.S. PATENT DOCUMENTS

| | | |
|---|---|---|
| 5,236,714 A | 8/1993 | Lee et al. |
| 5,611,971 A * | 3/1997 | Maedera et al. ............ 264/4.1 |
| 6,124,282 A | 9/2000 | Sellers et al. |
| 6,280,771 B1 | 8/2001 | Monkhouse et al. |
| 6,482,440 B2 * | 11/2002 | Zemlan et al. ............ 424/489 |
| 6,696,088 B2 | 2/2004 | Oshlack et al. |
| 6,725,118 B1 * | 4/2004 | Fried et al. ................ 700/118 |
| 2002/0107259 A1 * | 8/2002 | Burch et al. ................ 514/282 |
| 2003/0091635 A1 | 5/2003 | Baichwal et al. |
| 2003/0118641 A1 | 6/2003 | Maloney et al. |
| 2003/0124061 A1 | 7/2003 | Roberts |
| 2004/0052731 A1 | 3/2004 | Hirsh et al. |
| 2004/0058946 A1 | 3/2004 | Buchwald et al. |
| 2004/0110781 A1 | 6/2004 | Harmon et al. |
| 2004/0131552 A1 | 7/2004 | Boehm |
| 2004/0241218 A1 | 12/2004 | Tavares et al. |

FOREIGN PATENT DOCUMENTS

WO    WO 01/58451    8/2001

OTHER PUBLICATIONS

Journal of Oncology, 2002;20(9):2409-2410.*
Kaplan et al. Journal of Pharmacology and Experimental Therapeutics, 1997, 281(1):103-108.*
Weinhold, et al., "Buprenorphone Alone and in Combination with Naloxone in Non-Dependent Humans," Drug and Alcohol Dependence 30:263-274 (1992).
Mendelson, et al., "Buprenorphone and Naloxone Interactions in Opiate-Dependent Volunteers", Clin. Pharm. Ther. 60:105-114 (1996).
Patt, et al., "Using Controlled-Release Oxycodone for the Management of Chronic Cancer and Noncancer Pain", The American Pain Society Bulletin 6(4) (Jul./Aug. 1996).

* cited by examiner

*Primary Examiner*—San-ming Hui
(74) *Attorney, Agent, or Firm*—Sutherland Asbill & Brennan LLP

(57) ABSTRACT

A combination of a pro-agonist first medication in timed release form, and a sequestered second non-antagonist medication allows the first medication to be effective if taken according to medical directions. If the combination is tampered with or otherwise taken in a manner not according to medical directions, the second medication is released and prevents the first medication from becoming effective. The non-antagonist second medication does not precipitate immediate withdrawal in a dependent patient.

25 Claims, 1 Drawing Sheet

MATERIAL FOR CONTROLLING DIVERSION OF MEDICATIONS

FIELD OF THE INVENTION

The field of the invention is the field of controlling illicit diversion of medication.

BACKGROUND OF THE INVENTION

U.S. Pat. No. 6,969,088, which issued Feb. 24, 2004, and is entitled "Tamper-Resistant Oral Opioid Agonist Formulations," and U.S. Patent Application Publication No. 2004/0131552, by Boehm, which published Jul. 8, 2004, and is entitled "Sequestering Subunit and Related Compositions and Methods," discuss the problems and partial solutions to diversion of legal medications.

OBJECTS OF THE INVENTION

It is an object of the invention to produce a material for delivering medication to a patient, wherein the medication is effective if taken according to medical directions, and wherein the medication is ineffective if taken in a manner contrary to medical directions, and wherein the material causes no harm to a patient dependent on medication, even if taken in a manner contrary to medical directions.

SUMMARY OF THE INVENTION

The material of the invention contains a time release pro-agonist first medication admixed with a normally unabsorbed second medication which, if it were absorbed in the body of a patient, would prevent the conversion of the first medication to a more potent agonist metabolic byproduct. When the material is taken according to medical directions, the second medication is blocked from absorption in the body, and when the material is taken contrary to medical directions such as grinding or chewing the material, the second medication is released for absorption in the body, and prevents the pro-agonist from converting to a more metabolically active agonist material.

DETAILED DESCRIPTION OF THE INVENTION

Figure 1:
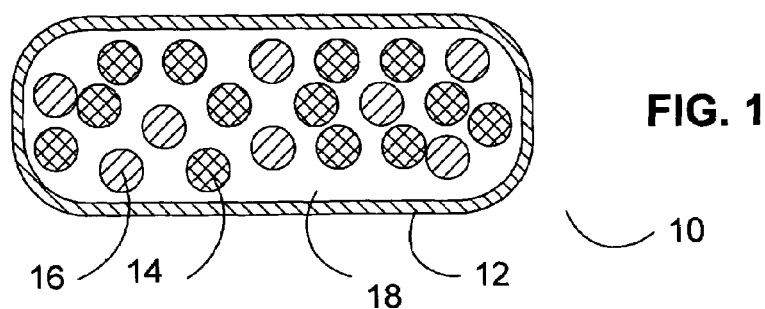
FIG. 1 shows a sketch of one embodiment of the invention.

Although opioids, such as morphine and hydromorphone are effective in the management of pain, there has been an increase in their abuse by individuals who are psychologically dependent on opioids or who misuse opioids for non-therapeutic reasons. Previous experience with therapeutic agents such as opioids has demonstrated a somewhat decreased abuse potential when opioids are administered in combination with a narcotic antagonist, especially in patients who are ex-addicts (Weinhold et al., Drug and Alcohol Dependence 30:263-274 (1992); and Mendelson et al., Clin. Pharm. Ther. 60:105-114 (1996)). These combinations, however, do not contain the opioid antagonist that is in a sequestered form. Rather, the opioid antagonist is released in the gastrointestinal system when orally administered and is made available for absorption, relying on the physiology of the host to metabolize differentially the agonist and antagonist and blocking of opiate receptors by the antagonist to negate the agonist effects.

International Patent Application No. PCT/US01/04346 (WO 01/58451) to Euroceltique, S. A., describes the use of a pharmaceutical composition that contains a substantially non-releasing opioid antagonist and a releasing opioid agonist as separate subunits that are combined into a pharmaceutical dosage form, e.g., tablet or capsule. However, because the agonist and antagonist are in physically separate compartments, they can be readily separated. Further, providing the agonist and antagonist as separate compartments, tablets are more difficult to form due to the mechanical sensitivity of some subunits comprising a sequestering agent.

The therapeutic agent can be any medicament. Preferably, the therapeutic agent is one that is addictive (physically and/or psychologically) and typically leads to abuse. In this regard, the therapeutic agent can be an opioid agonist. By "opioid" is meant to include a drug, hormone, or other chemical or biological substance, natural or synthetic, having a sedative, narcotic, or otherwise similar effect(s) to those containing opium or its natural or synthetic derivatives. By "opioid agonist," and "agonist" sometimes used herein interchangeably with terms "opioid" and "opioid analgesic," is meant to include one or more opioid agonists, either alone or in combination, and is further meant to include the base of the opioid, mixed or combined agonist-antagonists, partial agonists, pharmaceutically acceptable salts thereof, stereoisomers thereof, ethers thereof, esters thereof, and combinations thereof.

By "antagonist of a therapeutic agent" is meant any drug or molecule, naturally-occurring or synthetic, that binds to the same target molecule (e.g., a receptor) of the therapeutic agonist agent, yet does not produce a therapeutic, intracellular, or in vivo response. In this regard, the antagonist of a therapeutic agent binds to the receptor of the therapeutic agent, thereby preventing the therapeutic agent from acting on the receptor, thereby preventing the achievement of a "high" in the host. Naloxone is an example of a well known opioid antagonist.

An unrecognized problem with the above identified patents or publications dealing with a time released opioid agonist admixed with a normally sequestered opioid antagonist is that a patient who is physically dependent on opioid drugs will go into "precipitated withdrawal" and could become violently and possibly dangerously ill if an opioid antagonist is administered. Depending upon the drug upon which dependence has been established and the duration of use and dose, symptoms of withdrawal vary in number and kind, duration and severity. The most common symptoms of the withdrawal syndrome include anorexia, nausea, pupillary dilation, chills alternating with excessive sweating, abdominal cramps, nausea, vomiting, muscle spasms, hyper-irritability, lacrimation, rhinorrhea, goose flesh and increased heart rate. Natural abstinence syndromes typically begin to occur 24-48 hours after the terminating the opioid agonist, reach maximum intensity about the third day and may not begin to decrease until the third week. Precipitated abstinence syndromes produced by administration of an opioid antagonist vary in intensity and duration with the dose and the specific antagonist, but generally vary from a few minutes to several hours in length. Such a patient could engage in dangerous, criminal behavior in a desperate and attempt to obtain drugs to reverse the precipitated withdrawal syndrome. Furthermore, the experience of withdrawal is through to strengthen the desire to obtain opiates in the future and thereby could worsen the patient's opiate addition.

In a preferred embodiment of the present invention, a time released pro-agonist medication is combined with a normally sequestered medication which prevents the conversion of the pro-agonist medication in the body to a metabolic byproduct which is a substantially more potent agonist. When a patient takes the medication according to medical directions, for example by swallowing the tablet, pill, or capsule whole, the normally sequestered medication passes through the body without absorption and has no effect. The time released pro-agonist medication is released over time in the body of the patient and converted to an agonist metabolite, which is effective and long lasting.

When the tablet, pill or capsule is chewed, ground, or otherwise treated contrary to medical instructions to make the entire dose of pro-agonist medication available for immediate absorption and use in the body, the normally sequestered medication is also liberated from the sequestering means and is also immediately available for absorption into the body. The normally sequestered medication is not in itself an opioid antagonist, and does not precipitate withdrawal in a dependent patient. The liberated, normally sequestered medication, however, blocks conversion of some of the pro-agonist material to the more potent agonist form, and there is an unsatisfying response felt by the opiate tolerant, addicted person.

The most preferred embodiments of the invention use hydrocodone or oxycodone as the pro-agonist medication. Hydrocodone and oxycodone (in time release form having brand name OxyContin®) are often referred to as agonists or opioid agonists. However, oxycodone is converted, in the body, by the 2D6 component of the P450 metabolic system, to a metabolite oxymorphone, which is at least 10 times as effective as oxycodone as an agonist, as noted in an article by Richard B. Patt in The American Pain Society Bulletin 6 (4), JULY/AUGUST 1996, which is available on the web at (http://www.ampainsoc.org/pub/bulletin/jul96/innovate.htm).

The most preferred embodiment of the present invention is to incorporate a strong 2D6 inhibitor in a sequestered form in the capsule, which would be released upon tampering, and will minimize or prevent the desired euphoriant response. There will be little associated precipitation of opiate withdrawal.

Among agents that are strong inhibitors of 2D6 are: ajmalicine and other Rauwolfia alkaloids; chloroquine; mepyramine; cimetidine; ketoconazole; macrolides; quinidine; fluoxetine (and its metabolite norfluoxetine); reserpine; paroxetine; and fluvoxamine. Fluvoxamine is an FDA approved, safe medication, which is the most preferred medication, but other compounds are anticipated by the inventor which are equally or more effective. Such additional compounds will be found by ordinary experimentation by one of ordinary skill in the art.

In the present specification, a molecule which is a less potent agonist than its metabolite is defined as a "pro-agonist", even if the pro-agonist molecule has some agonist activity. The inventor anticipates that other pro-agonist medications will work effectively when combined with presently known or other inhibitors which will be found by ordinary experimentation. The inventor anticipates that the most effective combination will be the combination in which there is a very large difference in agonist activity between the pro-agonist medication and its more potent agonist metabolite. It is known, for example, that proenkephalin, prodynorphin, and pro-opiomelanocortin are inactive precursors from which the active opioid peptides MET-ENK and LEU-ENK, LEU-ENK, DYN A and DYN B, and beta endorphin and MET-ENK respectively, are derived in the body by cutting the precursor will specific peptidase enzymes (which hydrolyze bonds between amino acids). The inventor anticipates that inhibition of the action of such specific peptidase enzymes is possible and may be reduced to practice in a short time by ordinary experimentation as is known to one of skill in the art.

To increase the deterrent effect, a time-release pro-agonist produce package of a preferred embodiment of the invention carries an explicit instruction that tampering renders the drug ineffective.

FIG. 1 shows a sketch of one embodiment of the invention, wherein a capsule, pill or table 10 conveys the material of the invention. An optional outer covering 12, such as a capsule covering, encases microcapsules 14 and 16, each containing a different medication. An optional filler material 18 is shown.

Figure 2:
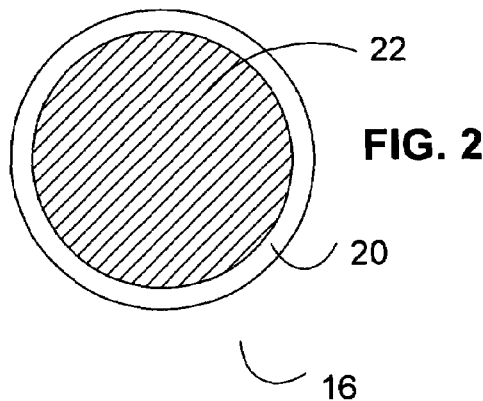
FIG. 2 shows one of the microcapsules of FIG. 1 in more detail.

FIG. 2 shows one of the microcapsules 16 in more detail. An outer coating 20 encapsulates the first pro-agonist medication 22 of the invention. The outer coating 20 dissolves in vivo and releases the drug 22 in a certain time. Depending on the outer coating 20, the medication 22 may be released faster or slower than the medication 22 in other microcapsules 16. Although FIG. 2 shows a microcapsule 16 having a separate interior holding the pro-agonist medication, preferred embodiments of the invention use any of the known or yet to be invented ways of time releasing medications. Those ways known in the present art also include dual matrix polymers and dendritic polymer formulations.

Figure 3:
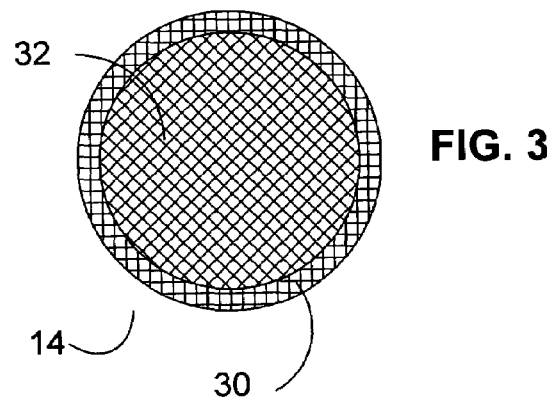
FIG. 3 shows another of the microcapsules of FIG. 1 in more detail.

FIG. 3 shows one of the microcapsules 14 encapsulating a second medication 32 of the invention. The outer coating 30 of the microcapsule 14 is normally not dissolved in the digestive system of the patient, and the medication 32 passes through the digestive system with no effect. However, if the capsule 10 is ground, chewed, or otherwise tampered with the medication 32 is released when the material is ingested, and the medication 32 blocks conversion of the pro-agonist medication 22 to an agonist metabolite.

In a preferred embodiment of the invention, microcapsules 14 and 16 have the same specific density, so that separating microcapsules 14 and 16 by settling or centrifuging is hindered.

In a preferred embodiment of the invention, microcapsules 14 and 16 have coatings which have similar flocculation properties, so that separation by flocculation is hindered.

In a preferred embodiment of the invention, microcapsules 14 and 16 have coatings which have similar properties to hinder other separation technologies as are known in the art.

In a preferred embodiment of the invention, filler material 18 comprises a material which inactivates the pro-agonist medication 22 is the coating 20 is chemically dissolved in vitro instead of in vivo. The inactivation is possible because the pro-agonist medication 22 is usually absorbed from the digestive system into the blood in a time ($t_1$) of minutes once the protective coating is dissolved, and a person tampering with the medication must wait a much longer time ($t_2$) until a significant portion of the microcapsules 16 have released their medication 22 before he or she can separate out the medication 22. In this time (t), the medication 22 has a greater chance of reacting with the filler material 18 in vitro than it would have in vivo. Thus, the medication 22 will be effective if taken according to medical direction, and would be much less effective if tampered with in vitro.

Although FIG. 3 shows a microcapsule 14 having a separate interior holding a blocking medication 22 for blocking the pro-agonist medication and an exterior coating 30 which does not generally permit the release of the medication 22, preferred embodiments of the invention use any of the known or yet to be invented ways of encapsulating or sequestering medications for a time sufficient to pass the medication through the digestive tract. Those known in the present art also include dual matrix polymers and dendritic polymer formulations.

All of the patents, patent applications, and references noted above are hereby included in their entirety, including references.

Obviously, many modifications and variations of the present invention are possible in light of the above teachings. It is therefore to be understood that, within the scope of the appended claims, the invention may be practiced otherwise than as specifically described.

I claim:

1. A pharmaceutical dosage form comprising:
   a first plurality of microcapsules, each microcapsule of the first plurality containing a pro-agonist medication in a controlled release form, the pro-agonist medication being metabolizable in vivo to an agonist following administration of the pharmaceutical dosage form to a human; and
   a second plurality of microcapsules which comprise a second medication in a sequestered form such that the second medication is not absorbed in vivo following said administration of the pharmaceutical dosage to the human according to medical direction, the second plurality of microcapsules being admixed with the first plurality of microcapsules;
   wherein the second medication is one which will block conversion of the pro-agonist medication to the agonist if the pharmaceutical dosage form is altered to liberate the second medication from its sequestration.

2. The pharmaceutical dosage form of claim 1, wherein the pro-agonist medication is one which is converted in the body by the 2D6 component of the P450 metabolic system to the agonist.

3. The pharmaceutical dosage form of claim 1, wherein the pro-agonist medication comprises an opioid.

4. The pharmaceutical dosage form of claim 1, wherein the pro-agonist medication comprises hydrocodone.

5. The pharmaceutical dosage form of claim 1, wherein the second medication comprises an inhibitor of the 2D6 component of the P450 metabolic system.

6. The pharmaceutical dosage form of claim 5, wherein the second medication comprises fluoxetine.

7. The pharmaceutical dosage form of claim 1, wherein the second medication comprises fluoxetine, reserpine, paroxetine, or a combination thereof.

8. The pharmaceutical dosage form of claim 1, which is a tablet or capsule containing the first and second pluralities of microcapsules.

9. The pharmaceutical dosage form of claim 1, wherein the microcapsules of the first plurality and of the second plurality have approximately the same density.

10. The pharmaceutical dosage form of claim 1, wherein the microcapsules of the first plurality and of the second plurality have approximately the same flocculation characteristics.

11. The pharmaceutical dosage form of claim 1, wherein the microcapsules of the first plurality and of the second plurality have approximately the same color, size, and textural appearance.

12. The pharmaceutical dosage form of claim 1, further comprising one or more matrix materials.

13. The pharmaceutical dosage form of claim 12, wherein the matrix material comprises a bioerodible or biodegradable polymer.

14. The pharmaceutical dosage form of claim 1, wherein the first plurality of microcapsules further comprise a filler material which inactivates the pro-agonist medication if the pharmaceutical dosage form is dissolved in vitro.

15. The pharmaceutical dosage form of claim 1, wherein the microcapsules of the second plurality of microcapsules include a layer of non-biodegradable material which covers the second medication.

16. An oral pharmaceutical dosage form comprising:
    an opioid pro-agonist medication in a controlled release form, the pro-agonist medication being metabolizable in vitro to its agonist form following administration of the pharmaceutical dosage form to a human; and
    a second medication in a sequestered form such that the second medication is not available for absorption in vivo following oral administration of the pharmaceutical dosage to the human according to medical direction;
    wherein the second medication will block metabolic conversion of the opioid pro-agonist medication to its agonist form if the pharmaceutical dosage form is altered to liberate the second medication from its sequestration.

17. The pharmaceutical dosage form of claim 16, wherein the opioid pro-agonist medication is one which is converted in the body by the 2D6 component of the P450 metabolic system to the agonist.

18. The pharmaceutical dosage form of claim 17, wherein the second medication comprises an inhibitor of the 2D6 component of the P450 metabolic system.

19. The pharmaceutical dosage form of claim 16, wherein sequestration of the second medication comprises the second medication being encapsulated by or dispersed with a material that does not dissolve or degrade in vivo following oral administration.

20. The pharmaceutical dosage form of claim 16, wherein the opioid pro-agonist medication comprises hydrocodone and the second medication comprises fluoxetine.

21. The pharmaceutical dosage form of claim 16, further comprising a filler material which inactivates the opioid pro-agonist medication if the pharmaceutical dosage form is dissolved in vitro.

22. A tablet or capsule comprising:
    opioid pro-agonist medication particles coated by or dispersed in a degradable matrix material which provides controlled release in vivo, the pro-agonist medication being metabolizable in vivo to its agonist form following administration of the tablet or capsule to a human; and
    a second medication coated by or dispersed in a non-degradable material, which provides that the second medication is not available for absorption in vivo following oral administration of the tablet or capsule to the human according to medical direction;
    wherein the second medication is one which will block conversion of the opioid pro-agonist medication to the agonist if the tablet or capsule is altered to liberate the second medication from the non-degradable material.

23. The tablet or capsule of claim 22, wherein the opioid pro-agonist medication is one which is converted in the body by the 2D6 component of the P450 metabolic system to the agonist.

24. The tablet or capsule of claim 22, wherein the second medication comprises an inhibitor of the 2D6 component of the P450 metabolic system.

25. The tablet or capsule of claim 22, wherein the opioid pro-agonist medication comprises hydrocodone and the second medication comprises fluoxetine.

* * * * *